(12) United States Patent
Kulkarni et al.

(10) Patent No.: US 8,797,551 B2
(45) Date of Patent: Aug. 5, 2014

(54) COMPACT, AFFORDABLE OPTICAL TEST, MEASUREMENT OR IMAGING DEVICE

(75) Inventors: Manish D Kulkarni, Pleasanton, CA (US); Shuqing Ma, San Jose, CA (US); Balasigamani Devaraj, Morgan Hill, CA (US)

(73) Assignee: Netra Systems Inc, Pleasanton, CA (US)

(*) Notice: Subject to any disclaimer, the term of this patent is extended or adjusted under 35 U.S.C. 154(b) by 537 days.

(21) Appl. No.: 12/941,991

(22) Filed: Nov. 8, 2010

(65) Prior Publication Data

US 2011/0273721 A1 Nov. 10, 2011

Related U.S. Application Data

(60) Provisional application No. 61/259,294, filed on Nov. 9, 2009.

(51) Int. Cl.
*G01B 9/02* (2006.01)

(52) U.S. Cl.
USPC .......................................... 356/521

(58) Field of Classification Search
USPC .................. 356/479, 497, 521, 488, 494, 499
See application file for complete search history.

(56) References Cited

U.S. PATENT DOCUMENTS

| | | | |
|---|---|---|---|
| 7,126,693 B2* | 10/2006 | Everett et al. | 356/479 |
| 7,940,398 B2* | 5/2011 | Ohbayashi et al. | 356/479 |
| 2005/0231727 A1* | 10/2005 | Podoleanu et al. | 356/479 |
| 2007/0024856 A1* | 2/2007 | Izatt et al. | 356/456 |
| 2007/0024868 A1* | 2/2007 | Izatt et al. | 356/511 |
| 2010/0157308 A1* | 6/2010 | Xie | 356/477 |

* cited by examiner

*Primary Examiner* — Jonathan Hansen
(74) *Attorney, Agent, or Firm* — Geeta Kadambi; Riddhi IP LLC (57) ABSTRACT

The system disclosed is for optical coherence tomography (OCT). The system includes an improved interferometric system for metrology, detection, ranging as well as imaging system based on optical coherence tomography (OCT). Further, the method provides advancements in detection, imaging of samples in biological, medical, ophthalmic, corneal and retinal diagnosis.

2 Claims, 7 Drawing Sheets

COMPACT, AFFORDABLE OPTICAL TEST, MEASUREMENT OR IMAGING DEVICE

CROSS-REFERENCE TO RELATED APPLICATIONS

This patent application claims the priority filing date of the provisional U.S. patent application (Application No. 61/259,294) titled "A novel compact, affordable optical test, measurement or imaging device," filed on Nov. 9, 2009 by the inventors Balasigamani Devaraj, Manish Dinkarrao Kulkarni and Shuqing Ma. This benefit is claimed under 35. U.S.C. §119 and the entire disclosure of the Provisional U.S. patent Application No. 61/259,294 is incorporated here by reference.

FIELD OF THE INVENTION

The present invention relates to the field of optical measurement devices. More particularly, the present invention relates to the field of optical test & measurement, interferometry, optical ranging and imaging, of a specimen using optical coherence tomography.

BACKGROUND OF THE INVENTION

Optical imaging of a specimen such as a biological specimen has always been a formidable and challenging task because the complex microscopic structure of tissues causing strong scattering of the incident radiation. The invention of confocal microscopy and its advanced development in the past few years have provided the researcher the capability to study biological specimens including living organisms without the need for tissue resection and histological processing. However, the presence of multiple scattering in samples limits confocal microscopy to specimens which are thin and mostly transparent. There is a need, therefore, for new optical methods capable of in vivo imaging deeper inside highly scattering tissues and other biological specimens.

Optical coherence tomography ("OCT") is a technology that allows for noninvasive, cross-sectional optical imaging in biological media with high spatial resolution and high sensitivity. OCT is an extension of low coherence or white-light interferometry, in which a low temporal coherence light source is utilized to obtain precise localization of reflections internal to a probed structure along an optic axis (i.e., as a function of depth into the sample). OCT delivers high resolution because it is based on light, rather than sound or radio frequency. An optical beam is directed at the tissue, and a small portion of this light that reflects from sub-surface features is collected. In this, most of the light is not reflected but, rather, scatters. The scattered light has lost its original direction and does not contribute to forming an image but rather contributes to glare. Using the OCT technique, scattered light can be filtered out, completely removing the glare. Even the very tiny proportion of reflected light that is not scattered can then be detected and used to form the image. In the OCT instrument, an optical interferometer is used in such a manner as to detect only coherent light. In the process the depth and the intensity of the light reflected from a sub-surface feature is obtained. A three-dimensional image can be built by scanning, as in a sonar or radar system. The most commonly used interferometers in these devices are Michelson and Mach-Zehnder interferometer (MZI) which are well-known.

References [1, 2] report an interferometric system which comprises a Michelson Interferometer for imaging using OCT. The signal is detected by a grating based spectrometer equipped with a linear detector array (or a line-scan camera).

U.S. Pat. No. 7,443,514 discloses a system and method for using a spatial light modulator (SLM) which may be a GLV (Grating light valve, as described in reference 3), to perform a null test of an (aspheric) optical surface, where the system comprises a Michelson interferometer. If the input signal comprises of a broad-band-wavelength light, a grating light valve separates the light into light with narrow-band-wavelengths and outputs them sequentially at different time intervals in a single output fiber. A GLV is a type of a tunable filter.

In the above (U.S. Pat. No. 7,443,514) disclosed prior art, while the interferometer used is the Michelson Interferometer, the specimen tested is a non-living, highly controlled optical element, and no ranging (or OCT imaging) operation is performed. In contrast, our device will perform measurements in scattering specimens such as biological specimens and other non-living highly scattering specimens such as a sponge. Our device will also perform a ranging operation and OCT imaging in living and non-living specimens.

In U.S. Pat. Nos. 5,847,827 and 7,079,256 B2, the Mach-Zehnder interferometer (MZI) is built using bulk optical elements and uses time-domain form of optical-coherence-tomography. Spectral-domain OCT using MZI has not yet been reported.

Further, OCT interferometric systems known in the art are complex in arranging optical devices and expensive as well as not portable.

Accordingly, there is a need for compact, portable and economical interferometric system that works in reflection mode than transmission mode.

SUMMARY OF THE INVENTION

In view of the foregoing disadvantages inherent in the prior art, the general purpose of the present invention is to provide a novel compact, affordable optical test, measurement or imaging device that is configured to include all advantages of the prior art, and to overcome the drawbacks inherent therein.

An object of the present invention is to provide a novel compact, affordable optical test, measurement or imaging device used for detection, imaging of ocular structures and pathology in diagnostic, diagnosis and pathogenesis.

Another object of the present invention is to provide a spectral-domain interferometric system that comprises a Mach-Zehnder interferometer, and an optical system laterally scanning the specimen. Here and in the rest of the specifications, laterally scanning means scanning the beam in a direction perpendicular to the beam. Such a direction can be called x or y or any direction in x-y plane. Such lateral scanning provides multi-dimensional imaging as well as multi-dimensional metrology and multi-dimensional measurements. Lateral scanning can provide 2-dimensional or 3-dimennsional images. Lateral scanning can provide 2-dimensional or 3-dimennsional measurements. Lateral scanning can provide 2-dimensional or 3-dimennsional metrology. Such lateral scanning also permits optical coherence tomography (OCT) imaging.

Another object of the present invention is to provide an interferometric system that comprises a Mach-Zehnder interferometer, a frequency (ie., wavelength)-tunable detector and optionally a lateral scanning (of the specimen) mechanism. A tunable detector as defined in this invention comprises of a tunable filter (preceding the detector), which separates the input broad-band light into light with narrow-band-wavelengths and outputs them sequentially at different time intervals in a single output fiber.

In an aspect of the present invention, an interferometric system for imaging a biological sample is provided. The interferometric system comprises a broadband light source, a plurality of beam splitters, a plurality of minors, a sample, a lateral scanning optical system, a tunable filter, a detector and a data processing system.

In another aspect of the present invention, a method for generating a tomographic image of a sample is provided. The method includes a) light from the broadband light source which is operating at a suitable center wavelength enters into the interferometer where it gets separated into sample arm and reference arm using an optic beam splitter (B1). A light from the sample arm enters into the sample by means of lateral scanning optical system, and the back scattered light from the sample gets completely reflected at the beam splitter (B2) (99% R, 1% T) through lateral scanning optical system, and enters into beam splitter (B3) (99% T, 1% R). A light from the reference arm gets reflected by minor and reaches the beam splitter (B3). The light from the sample and reference arms, interfere each other at beam splitter (B3) before entering a tunable filter which wavelength-division-multiplexes the interfered light, and then finally enters into a detector for analysis. Wavelength-division-multiplexing as defined in this invention is a process of separating the input broad-band light into light with narrow-bands-with various center-wavelengths and outputting them sequentially at different time intervals in a single output fiber.

These together with the other aspects of the present invention, along with the various features of novelty that characterized the present invention, are pointed out with particularity in the claims annexed hereto and form a part of the present invention. For a better understanding of the present invention, its operating advantages, and the specified object attained by its uses, reference should be made to the accompanying drawings and descriptive matter in which there are illustrated exemplary embodiments of the present invention.

BRIEF DESCRIPTION OF THE DRAWINGS

Understanding of the present invention will be facilitated by consideration of the following detailed description of the preferred embodiments of the present invention taken in conjunction with the accompanying drawings, in which like numerals refer to like parts and in which.

DETAILED DESCRIPTION OF THE INVENTION

The present invention proposes an interferometric system, which is one of the major needs for refractive surgery, ophthalmic applications, corneal imaging, retinal imaging, endoscopic/catheter imaging etc. In particular, the invention is an integrated system for detection, ranging, metrology and multi-dimensional imaging.

Figure 1:
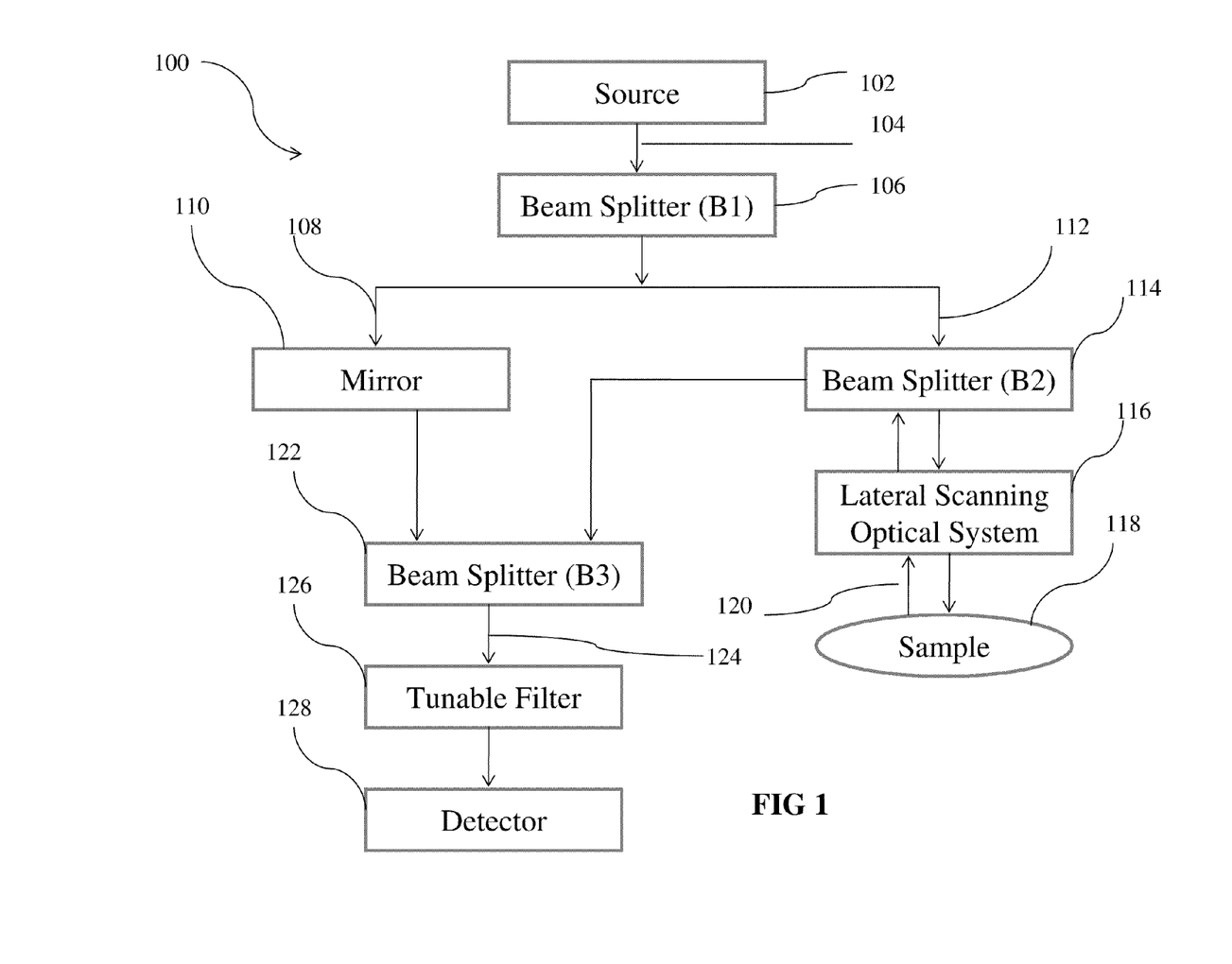
FIG. 1 is a flow chart illustrating an interferometric system configured with a wavelength-tunable filter such as a GLV (Grating light valve) to analyze the sample in accordance with an embodiment of the present invention.

Referring to FIG. 1 is a flow chart illustrating an Optical Coherence Tomography (OCT) measurement system configured with a tunable filter such as a GLV to analyze the sample in accordance with an embodiment of the present invention (100). As illustrated, methodology starts at step (102), wherein the source emits a beam of broadband light (104) which passes a first beam splitter (B1) (204) (typically 50/50) at step (106) getting divided into two separate light beams known as reference arm (108) and sample arm (112). At step (110) the reference arm (108) is reflected by a minor (M1) towards the third beam splitter (B3) (208) (typically 99% Transition and 1% Reflection) at step (122). The sample arm (112) is passed through a second beam splitter (B2) (206) (typically 99% reflection and 1% transmission) at step (114) which reflects the light to an optical delivery X-Y scanner system (212). In an embodiment, the optical delivery X-Y scanners system (212) may be a lateral scanning optical system, and the like. At step (116), the sample arm passes through lateral scanning optical system and falls upon the sample at step (118). The sample arm (112) is reflected back after it strikes the sample and is known as reflected sample arm (120). At step (116), the reflected sample arm (120) passes the lateral scanning optical system (212) and strikes the second beam splitter (B2) (206) at step (114). The second beam splitter (B2) (206) reflects the reflected sample arm (120) to the third beam splitter (B3) (208). At step (122), the reflected sample arm (120) strikes the third beam splitter (B3) (208). The reference arm (108) and reflected sample arm (120) interferes at step (122) after getting reflected from second beam splitter (B2) (206); known as interfered light beam (124), enters a tunable filter such as a grating light valve (GLV) (216) filter at step (126) where wavelength division multiplexing of interfered light beam (124) takes place. The multiplexed data enters a detector at step (128) and is further moved to a processor for processing of data. Wavelength-division-multiplexing as defined in this invention is a process of separating the input broad-band light into light with narrow-band-wavelengths and outputting them sequentially at different time intervals in a single output fiber.

Figure 2:
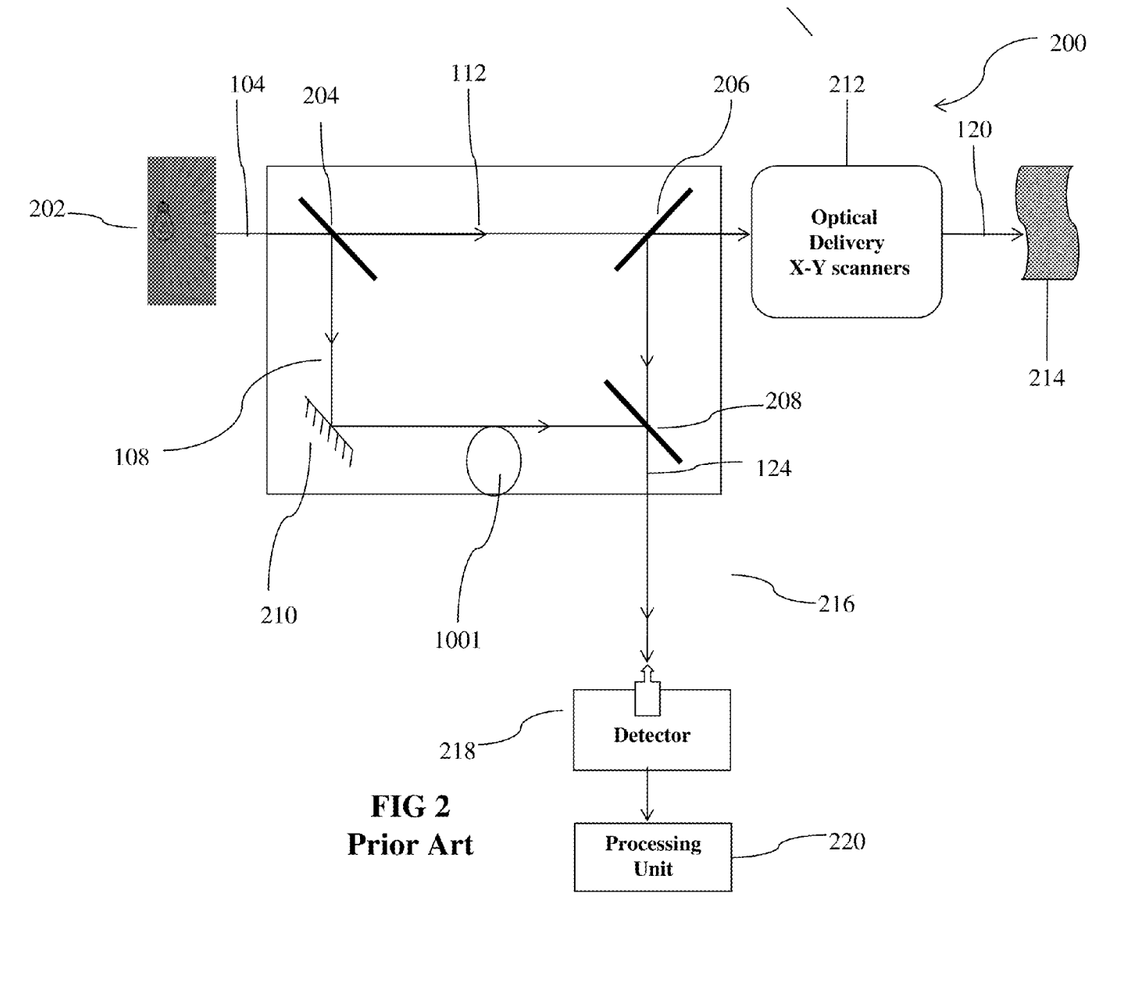
FIG. 2 illustrates an optical diagram of the Mach-Zehnder Interferometric system as known in the art.

According to one embodiment, the interferometer may be a Mach-Zhender interferometer used for analyzing data by wavelength-tuning or wavelength-division multiplexing. Mach-Zehnder interferometer (MZI) is an amplitude splitting interferometer. FIG. 2 is an optical diagram of the Mach-Zehnder Interferometric system that has known in the art.

Figure 3:
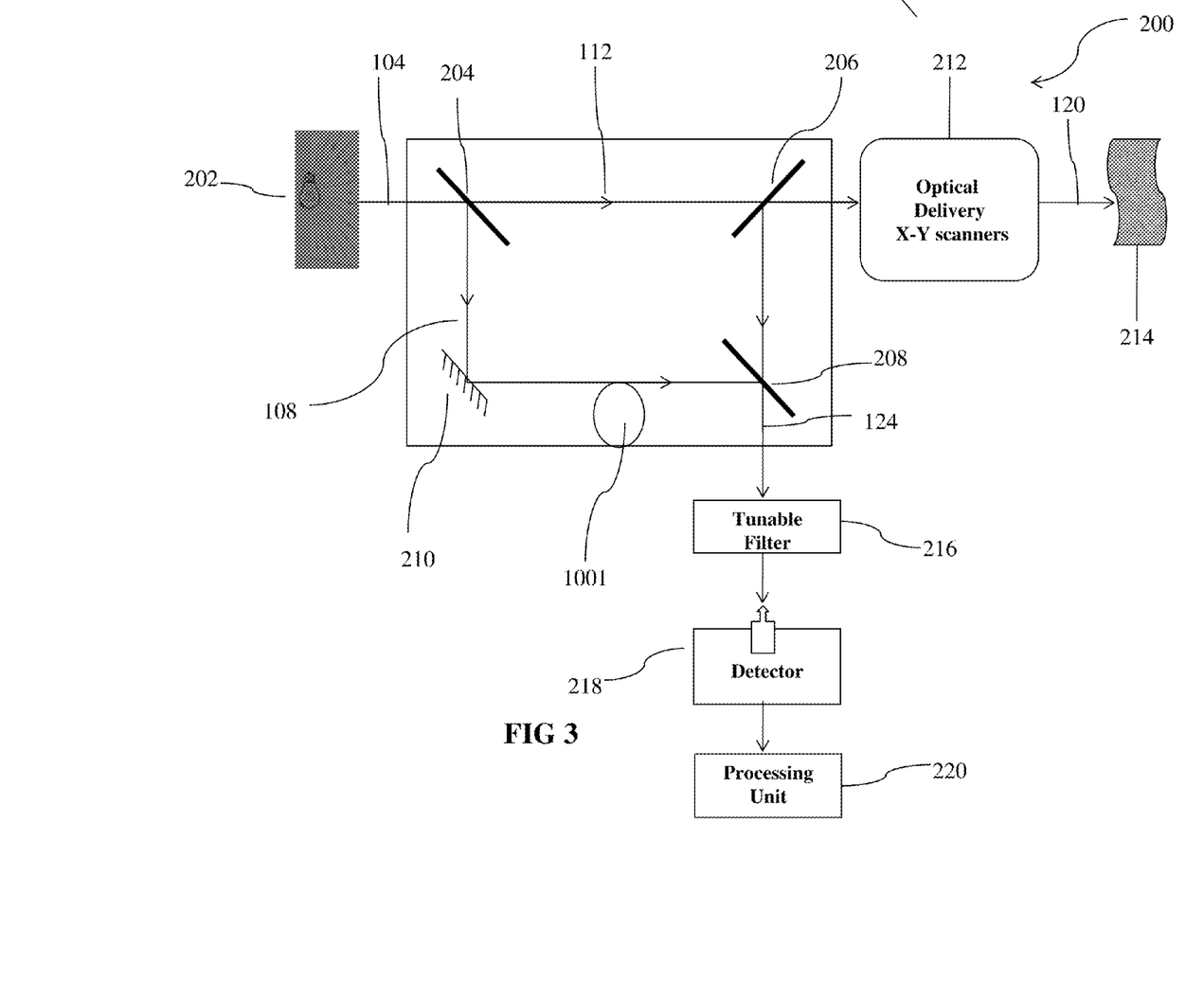
FIG. 3 illustrates an optical diagram of the Mach-Zehnder Interferometer configured with OCT system and a tunable filter such as a GLV in accordance with an embodiment of the present invention.

Referring to FIG. 3 is an optical diagram of the Mach-Zehnder Interferometer configured with OCT system and a wavelength tunable filter such as a GLV in accordance with an embodiment of the present invention. The MZI OCT system (200) having a light source (202) which emits a beam of broadband light (104). The beam of broadband light (104) is coupled with first beam splitter (B1) (204) which splits the beam in a typical (but not a must) ratio of 50:50. One half of the split beam is called reference beam; hereinafter termed as reference arm (108), and other half is sample beam; hereinafter termed as sample arm (112). The reference arm (108) is configured with a minor (M1) (210) which reflects the reference arm (108) to third beam splitter (B3) (208) having typically (but not limited to) 99% transmission and 1% reflection properties. The sample arm is configured with second beam splitter (B2) (206) typically (but not limited to) having 99% reflection and 1% transmission properties. According to one embodiment of the invention, a three port circulator may also be used in place of (B2) (206) and (B3) (208). The sample arm (112) is reflected to lateral scanning optical system (212) by second beam splitter (B2) (206) for further transferring it to the sample (214) which is placed outside the interferometer. The sample arm (112) is reflecting back to lateral Scanning Optical System (212) after striking the sample (214). It may also be termed as reflected sample arm (120) and is configured with the second beam splitter (B2) (206). The second beam splitter reflects the reflected sample arm (120) to third beam splitter (B3) (208). The reflected sample arm passes through the third beam splitter (B3) (208) and interferes with reference arm (108) reflecting from the minor (M1) (210). This interfered light beam (124) (as shown in FIG. 1), passed through a tunable filter (216) for multiplexing the data. According to another embodiment of the invention, the filter (216) used may be an acousto-optic tunable filter or a tunable interference filter or a grating-based filter or grating light valve (GLV) filter or a tunable Fabry-Perot interference filter, and the like. The multiplexed data are detected by a detector (218) and are forwarded to a data processing unit (220) for analyzing the data. A tunable filter as defined in this invention separates the input broad-band light into light with narrow-band-("tuned") wavelengths and outputs them sequentially at different time intervals in a single output fiber.

Figure 4:
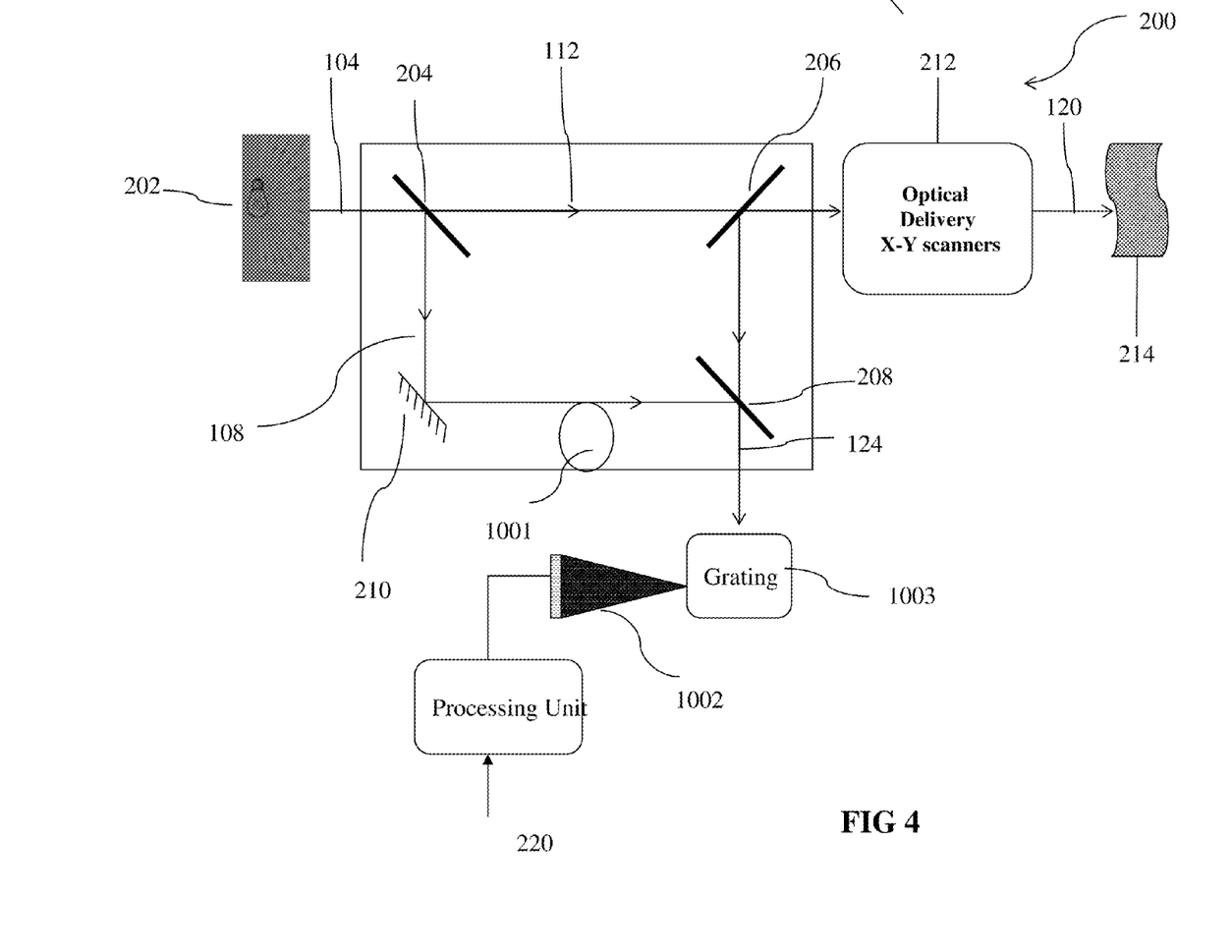
FIG. 4 illustrates an optical diagram of the Mach-Zehnder Interferometer configured with OCT system and a grating-spectrometer detection in accordance with an embodiment of the present invention.

According to one embodiment of the present invention, the light detection in the interferometer may be performed by a Grating spectrometer as shown in FIG. 4.

Figure 5:
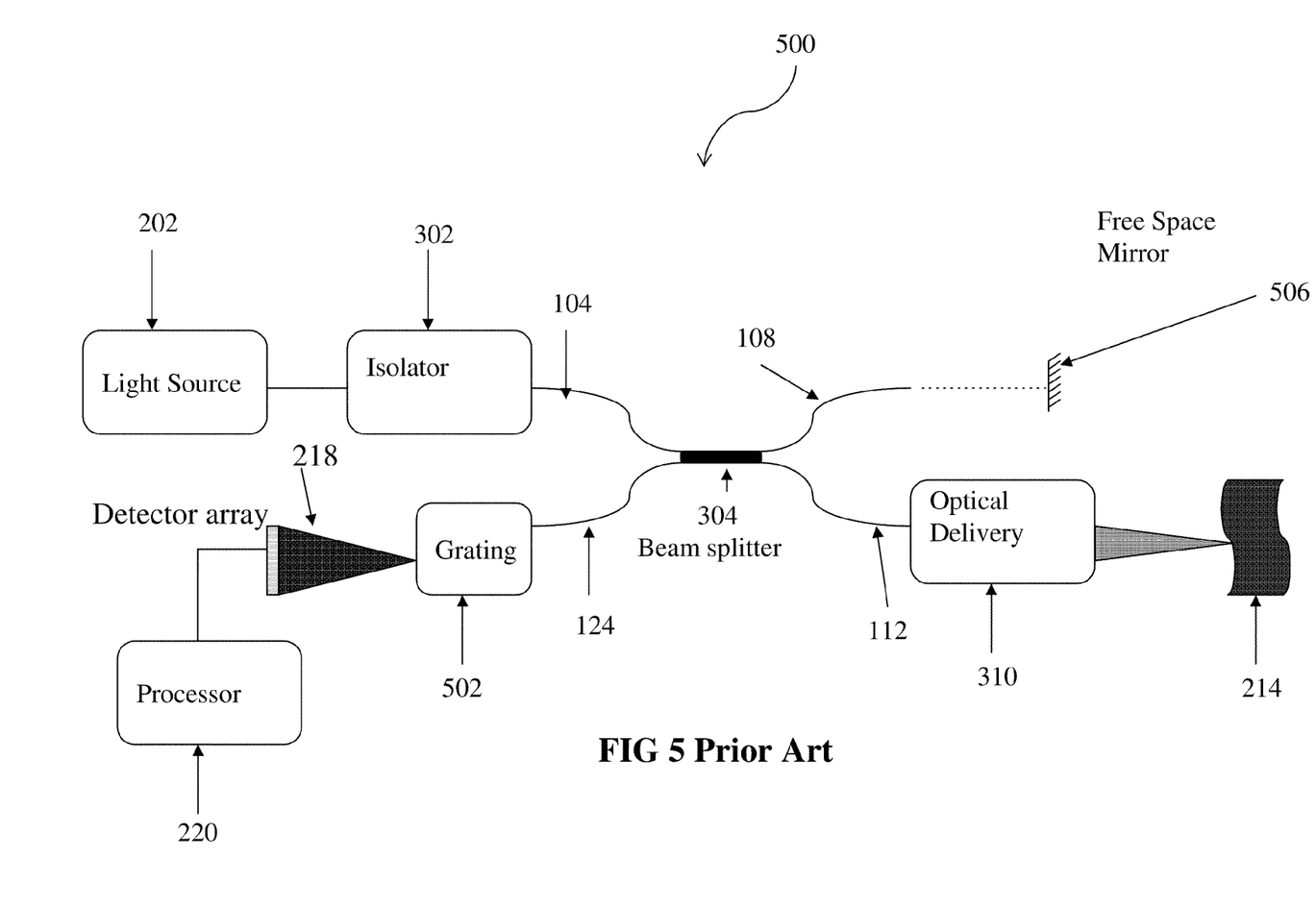
FIG. 5 illustrates an optical diagram of the Michelson Interferometric system as known in the art.

According to one embodiment, the interferometer may be a Michelson interferometer (MI) used for analyzing data by wavelength-division multiplexing or wavelength-tuning. Michelson interferometer (MI) is an amplitude splitting interferometer. FIG. 5 is an optical diagram of the Michelson Interferometric system that has known in the art.

Figure 6:
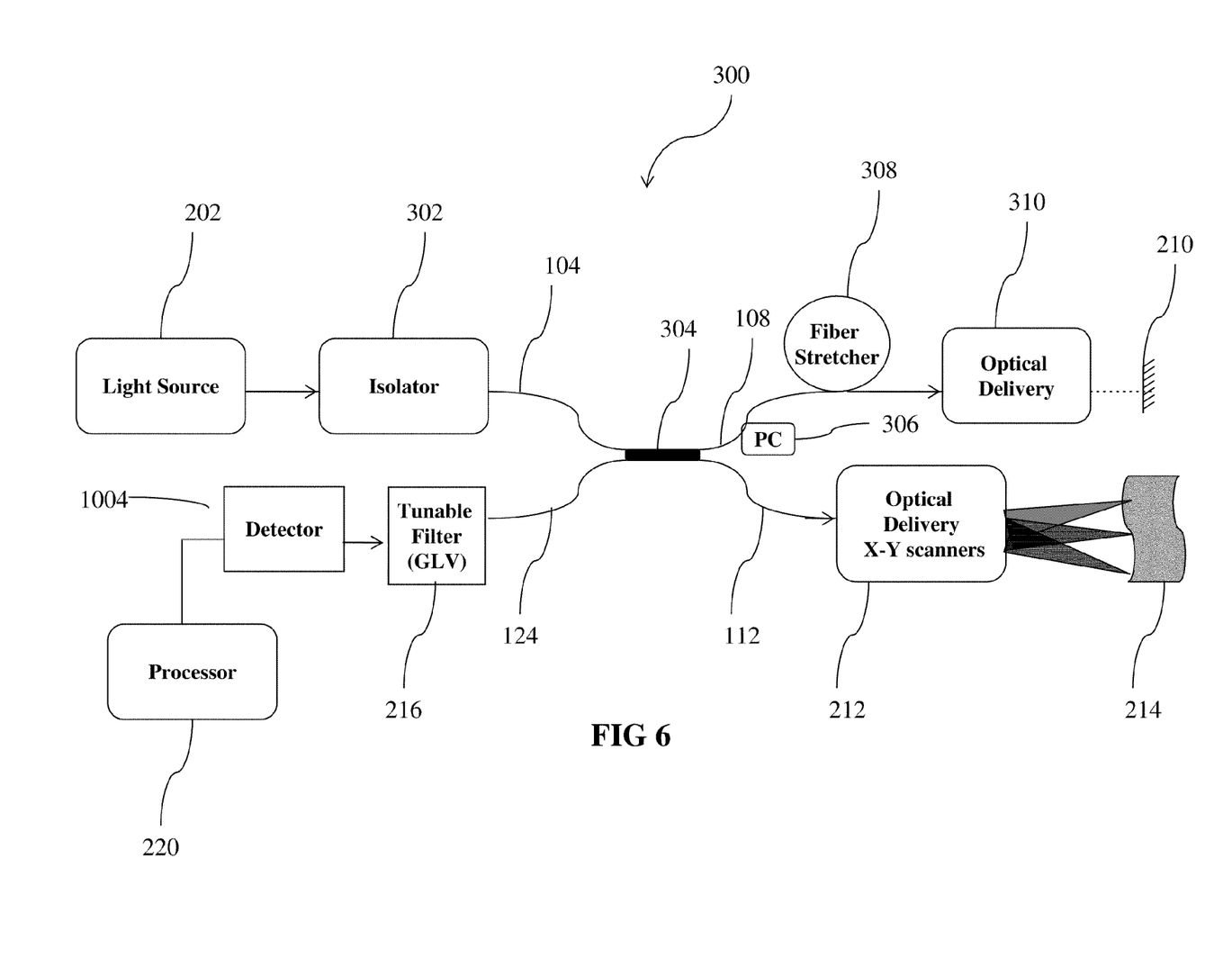
FIG. 6 illustrates an optical diagram of the Michelson Interferometer configured with OCT system and a tunable filter such as a GLV in accordance with an embodiment of the present invention.

Referring to FIG. 6 is an optical diagram of the Michelson Interferometer configured with OCT system and a tunable filter such as a GLV in accordance with an embodiment of the present invention. The interferometer (300) has source arm (202), reference arm (112), sample arm (108), and reflected sample arm (124). In this embodiment, a broad-band light source (202) operating at a suitable center wavelength is used. In the interferometer (300), the source light is separated into the sample and reference arms using a fiber optic beam splitter (204). The beam splitter is typically 50/50, but the same is not limiting the scope of the invention. The sample arm (108) consists of a probe, which focuses light into the sample (214) using lateral Scanning Optical System unit (212) and collects the backscattered light.

Figure 7:
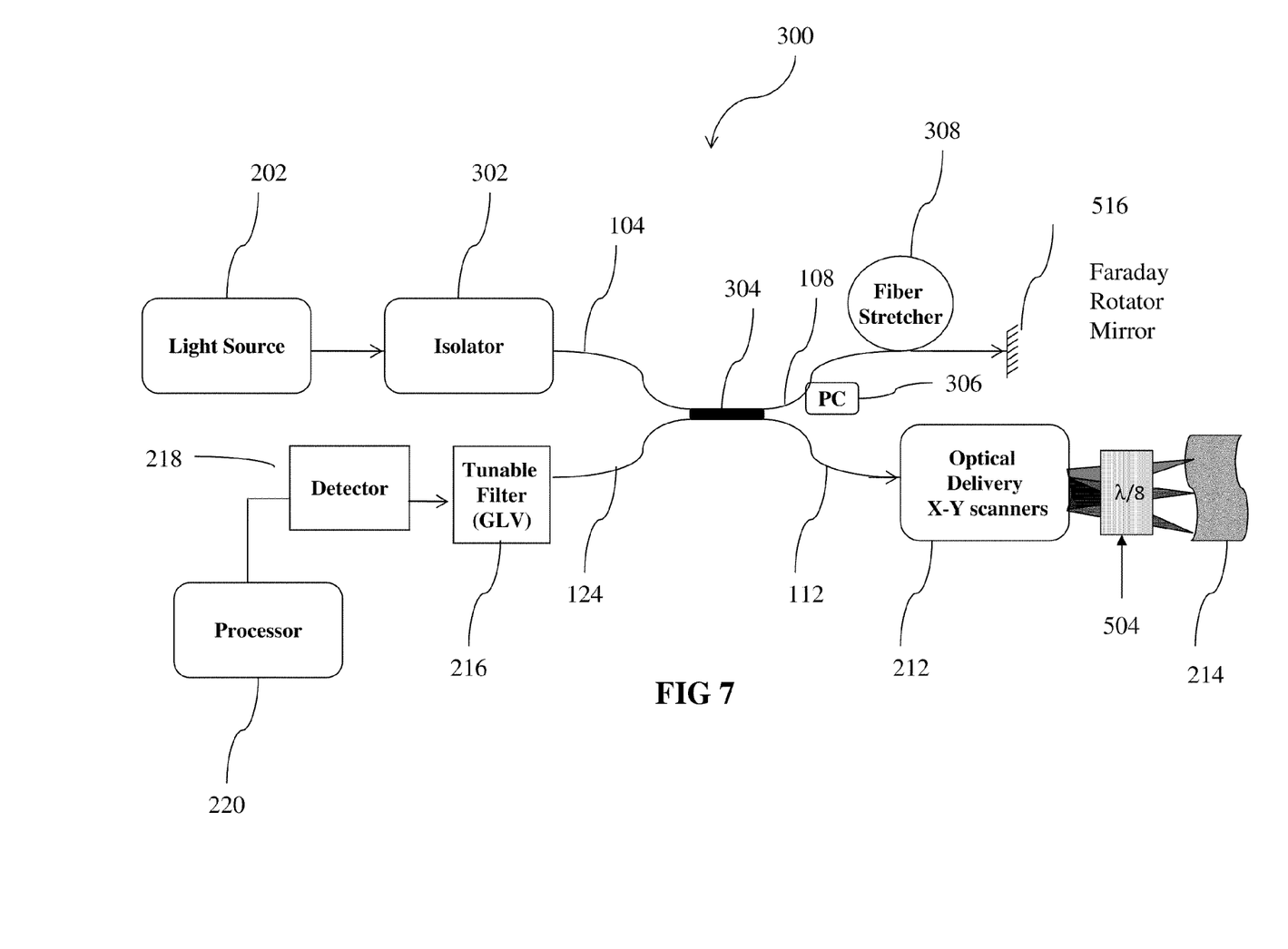
FIG. 7 illustrates an optical diagram of the Michelson Interferometer configured with OCT system and a tunable filter such as a GLV in accordance with an embodiment of the present invention.

A fiber-optically integrated Faraday Rotator mirror (506), may be appended at the end of the fiber in the reference arm (112) of the OCT interferometer system (300) as shown in FIG. 7. The waves reflected back from the sample arm (108) and the reference arm (112) interferes and enters into a tunable filter such as a GLV (216) for wavelength division multiplexing and is detected by the detector (1004) which is further sent to a processor (220) for processing the data. Since the interference signal is only created when the polarization in the reference arm (112) matches with that in the sample arm (108); in an embodiment, the rotation of a Faraday rotatory minor (506) may be 45 degrees and the same is not limiting the scope of the invention. In the sample arm (108) a [lambda]/8 waveplate (504) may be inserted just before the light incident on the sample (214). Since the polarization of the retroreflected light will be almost orthogonal to the incident light, the birefringence effects in the sample arm (112) of the interferometer (500) will get cancelled.

In some embodiments, the means to adjust polarization are used in the form of a fiber optic polarization compensator (PC) (306), which is made up of fiber optic loops, in the reference arm 112 to match the polarization in both the sample and reference arms. Such matching provides optimal interference signal strength.

REFERENCES

1. N. A. Nassif, B. Cense, B. H. Park, M. C. Pierce, S. H. Yun, B. E. Bouma, G. J. Tearney, T. C. Chen, J. F. de Boer "In vivo high-resolution video-rate spectral-domain optical coherence tomography of the human retina and optic nerve" 9 Feb. 2004/Vol. 12, No. 3/OPTICS EXPRESS 367
2. P. Andretzky, M. W. Lindner, J. M. Herrmann, A. Schultz, M. Konzog, F. Kiesewetter and G. Hausler, "Optical Coherence Tomography by "spectral radar": dynamic range estimation and in vivo measurements of skin" SPIE, Vol. 3567, 78-87, 1998
3. David M. Bloom, "The Grating Light Valve: revolutionizing display Technology" Proc. SPIE 3013, Projection Displays III, 165 (May 8, 1997); doi:10.1117/12.273868

What is claimed is:

1. A Mach-Zhender interferometric system for analyzing data of a sample by means of a tunable filter, comprising:
   a broadband light source which emits a beam of broadband light;
   a first beam splitter which splits the beam into a reference arm and a sample arm;
   a lateral scanning optical system to reflect the sample arm beam from a second beam splitter to the sample and reflecting back to the second beam splitter after striking the sample;
   a mirror configured to reflect the beam of the reference arm to a third beam splitter; the second beam splitter reflects the sample arm reflected from the sample to the third beam splitter;
   a tunable filter, resides in the front of a single detector, receives an interfered light beam formed by the combination of the reflected sample arm passing through the third beam splitter and the reference arm reflecting from the minor, wherein the tunable filter is a Grating light valve (GLV) filter; and
   a single detector detects a multiplexed data from the tunable filter and forwards the multiplexed data to a data processing unit for analyzing.

2. The interferometric system of claim 1, wherein the sample is a biological specimen.

* * * * *